US008196582B2

(12) United States Patent
Ogilvie

(10) Patent No.: US 8,196,582 B2
(45) Date of Patent: Jun. 12, 2012

(54) BACKPACK FOR AIR EXTRACTION FROM SNOW

(76) Inventor: Scott A. Ogilvie, Farmington, UT (US)

( * ) Notice: Subject to any disclaimer, the term of this patent is extended or adjusted under 35 U.S.C. 154(b) by 209 days.

(21) Appl. No.: 12/697,091

(22) Filed: Jan. 29, 2010

(65) Prior Publication Data

US 2010/0132702 A1 Jun. 3, 2010

Related U.S. Application Data

(63) Continuation of application No. 10/938,241, filed on Sep. 10, 2004, now Pat. No. 7,654,260.

(60) Provisional application No. 60/502,734, filed on Sep. 12, 2003.

(51) Int. Cl.

| | |
|---|---|
| ***A62B 7/10*** | (2006.01) |
| ***A62B 23/02*** | (2006.01) |
| ***A62B 19/00*** | (2006.01) |
| ***A62B 7/00*** | (2006.01) |
| ***A62B 9/00*** | (2006.01) |
| ***A62B 18/00*** | (2006.01) |
| ***A61M 15/00*** | (2006.01) |
| ***A61M 16/00*** | (2006.01) |

(52) U.S. Cl. .......... 128/205.27; 128/200.24; 128/201.25

(58) Field of Classification Search ............. 128/201.25, 128/204.17, 204.18, 205.27, 205.22, 205.21, 128/201.23, 202.19, 205.24, 206.29, 200.25, 128/200.28, 201.11, 201.26, 200.24; 2/744.8, 2/6.82, 205, 909, 171.3, 49.4, 906, 173, 410, 2/171, 182.8, 184.5, 209.7, 200.1, 10, 12, 2/413, 436, 421, 423–425, 411, 414

See application file for complete search history.

(56) References Cited

U.S. PATENT DOCUMENTS

| | | | |
|---|---|---|---|
| 2,861,568 | A | 11/1958 | Quilter et al. |
| 2,867,812 | A | 1/1959 | Roth et al. |
| 2,871,484 | A | 11/1959 | Finken et al. |
| 3,274,615 | A | 9/1966 | Merriam |
| 3,818,510 | A | 6/1974 | Romann |
| 4,078,561 | A | 3/1978 | Hanson |
| 4,141,086 | A | 2/1979 | Jackson |

(Continued)

FOREIGN PATENT DOCUMENTS

EP 0998959 A1 10/2000

OTHER PUBLICATIONS

Grissom, et al., "Respiration During Snow Burial Using an Artificial Air Pocket", Preliminary Communication, JAMA, May 3, 2000, vol. 283, No. 17.

(Continued)

*Primary Examiner* — Kristen Matter

(74) *Attorney, Agent, or Firm* — Kunzler Needham Massey & Thorpe

(57) ABSTRACT

An apparatus and system are disclosed to extract breathable air from snow via an air extraction backpack. The apparatus includes an air-permeable extraction assembly that is attached to a backpack. The air-permeable extraction assembly has an air intake cavity. An air-permeable membrane covers the air intake cavity. A mouthpiece is in fluid communication with the air intake cavity. The mouthpiece draws intake air through the air intake cavity upon inhalation by a user. A transfer guide passes intake air from the air-permeable extraction assembly to the mouthpiece upon inhalation by the user.

20 Claims, 5 Drawing Sheets

U.S. PATENT DOCUMENTS

| | | | | |
|---|---|---|---|---|
| 4,365,628 | A | 12/1982 | Hodel | |
| 4,434,514 | A | 3/1984 | Sundahl et al. | |
| 4,524,465 | A | 6/1985 | Huber | |
| 4,555,816 | A | 12/1985 | Broersma | |
| 4,627,115 | A | 12/1986 | Broersma | |
| 4,689,836 | A | 9/1987 | Vitaloni | |
| 4,729,132 | A | 3/1988 | Fierro | |
| 4,852,562 | A | 8/1989 | Howie | |
| 5,139,017 | A | 8/1992 | McCloud | |
| 5,490,501 | A | 2/1996 | Crowley | |
| 5,566,668 | A | 10/1996 | Jesadanont | |
| 5,758,639 | A | 6/1998 | Ikonen | |
| 5,784,724 | A | 7/1998 | Liang | |
| 5,829,065 | A | 11/1998 | Cahill | |
| 5,862,528 | A | 1/1999 | Saijo et al. | |
| 5,930,840 | A | 8/1999 | Arai | |
| 6,000,395 | A | 12/1999 | Brown | |
| 6,081,932 | A | 7/2000 | Kraemer | |
| 6,097,197 | A | 8/2000 | Matsuyama et al. | |
| 6,371,116 | B1 | 4/2002 | Resnick | |
| 6,405,728 | B1 * | 6/2002 | Van Hall et al. | 128/205.22 |
| 6,412,482 | B1 | 7/2002 | Rowe | |
| 6,644,308 | B2 | 11/2003 | Kalhok et al. | |
| 6,647,556 | B2 | 11/2003 | Grepper et al. | |
| 6,826,783 | B1 | 12/2004 | Grove et al. | |
| 6,931,671 | B2 | 8/2005 | Skiba | |
| 7,111,329 | B2 | 9/2006 | Stroud et al. | |
| 7,120,940 | B2 | 10/2006 | Fournier et al. | |
| 2001/0039674 | A1 | 11/2001 | Shida | |
| 2002/0104153 | A1 | 8/2002 | Benedict et al. | |
| 2002/0124298 | A1 | 9/2002 | Muskovitz | |
| 2005/0077135 | A1 * | 4/2005 | Drew et al. | 190/102 |
| 2007/0266482 | A1 | 11/2007 | Alexander et al. | |

OTHER PUBLICATIONS

Page et al., "Avalanche Deaths in the United States: a 45-Year Analysis", Wilderness and Environmental Medicine, 10, pp. 146-151 (1999).

Cindy Hirschfeld, "The Avalung: A Look at the Backcountry's Newest Player", Issue 21, 1999.

* cited by examiner

BACKPACK FOR AIR EXTRACTION FROM SNOW

CROSS-REFERENCES TO RELATED APPLICATIONS

This is a continuation application of and claims priority to U.S. patent application Ser. No. 10/938,241 entitled "Protective Helmet for Air Extraction from Snow" and filed on Sep. 10, 2004 for Scott A. Ogilvie, which is incorporated herein by reference. Patent application Ser. No. 10/938,241 claims the benefit of U.S. Provisional Patent Application No. 60/502,734 filed on Sep. 12, 2003.

BACKGROUND OF THE INVENTION

1. Field of the Invention

Embodiments of this invention relate to emergency breathing devices and more particularly relate to backpacks and protective helmets for air extraction from snow.

2. Description of the Related Art

In a typical avalanche accident, the snow accelerates to full speed and the snow mass usually comes to an abrupt halt in the run out zone. The snow packs tightly around the victim and sets up like concrete the instant the moving snow comes to a rest. A buried victim typically finds himself tightly encased in the heavy snow pack. Rarely can a fully buried victim escape this snow encasement by his own efforts.

In addition to being buried and immobilized, the victim's air supply is most often very limited. The victim may or may not have an air pocket in front of his face or surrounding his head. If the head is very near the surface or there is a hole from the head to the surface, the victim is very fortunate. More often than not, however, the facial air pocket is small or nonexistent. As the victim breathes within this small confined space, the oxygen is rapidly consumed and replaced by carbon dioxide. Within a short time, the lack of oxygen and/or the abundance of carbon dioxide may cause asphyxiation and/or suffocation.

Air diffusion, in which air may diffuse through the snow, between the snow pack and the air pocket helps to increase the time of breathable atmosphere. In some cases, air may diffuse from the surface of the snow pack, through the snow, to an air pocket near the victim's face. There is one phenomenon, however, which greatly limits the beneficial air diffusion between the snow pack and air pocket. This phenomenon is known as ice masking. Ice masking occurs when a person exhales warm, moist air into the small air pocket surrounding one's face, where the moisture condenses on the snow surface within the air pocket. After repeated breaths, the layer of moisture builds or thickens, greatly reducing the snow porosity at this boundary due to this accumulation of moisture. Unfortunately, the air within the nearby snow pack may become unavailable to the victim due to this moist snow layer. As a result, the victim rapidly suffocates and, if the victim is not located, unburied, and resuscitated, if necessary, the victim will die. After suffocation, the body temperature drops and the thick moist snow surrounding the face refreezes into what is commonly known as an ice mask. The thickness of this ice mask is a good indication of the length of time the victim remained alive before eventually suffocating.

Many devices have been contrived in an attempt to extend the breathing time of a fully buried avalanche victim. Some of these devices employ carbon dioxide absorbers to absorb and, thereby, reduce the amount of carbon dioxide that is exhaled and rebreathed. Unfortunately, these devices do not address the problems resulting from the limited air that may diffuse through the snow pack. Other devices employ oxygen tanks in order to provide additional oxygen to the victim in addition to or in place of the diffused air. However, these devices are both bulky and heavy and, therefore, inhibit the movement of the user in many of the recreational activities that draw the users to the mountains in the first place. Additionally, many of these devices employ one or more tubes that connect the mouthpiece to the oxygen tank, typically worn on the users chest or back. These tubes may easily be ripped away from the victim's mouth or the oxygen tank due to the forceful movements of the avalanching snow.

Another device, the AVALUNG, which is currently marketed in the United States and elsewhere, also employs a tube to bring air to the victim's mouth. The tube is connected to a type of air pouch that allows air to be drawn in from the surrounding snow pack. Versions of this device are used in jackets or on straps that may be worn as the outermost layer of clothing. In other words, the air pouch may be worn in an exterior compartment of the jacket. Alternatively, the air pouch may be strapped onto the victim via a contraption having a waist strap and a shoulder strap.

However, these pouches are typically located around the victim's stomach or chest area, requiring a long tube to transfer the inhaled air to the user's mouth. As described above, it may be difficult or even impossible to retain the mouthpiece in the user's mouth as the user is tossed about by the avalanching snow. Additionally, an avalanche victim may be swept away by an avalanche before engaging the mouthpiece. This may occur especially where the victim does not see the avalanche begin and/or where the victim does not have an audible warning, for example, due to the noise of heavy equipment or recreational machinery. Additionally, the surface area of the air pouch is typically small and limited by the costs of producing the device and possibly in order to not restrict the user's movement. The device also limits the user's dress because the device must be worn on top of all clothing and apparel worn by the user. The functionality of the device is nullified if it is worn, for example, under a jacket or obstructed by a piece of equipment, such as a backpack.

From the foregoing discussion, it should be apparent that a need exists for an apparatus, system, and method for air extraction from snow that are not subject to the same disadvantages and inconveniences. Beneficially, such an apparatus, system, and method would limit the requirement for long tubes that are likely to be torn away from the victim's mouth. The apparatus, system, and method also would advantageously be incorporated into existing equipment and maximize the amount of surface area used to draw in air diffused through the snow pack.

SUMMARY OF THE INVENTION

The present invention has been developed in response to the present state of the art, and in particular, in response to the problems and needs in the art that have not yet been fully solved by currently available breathing devices. Accordingly, the present invention has been developed to provide an apparatus and system to extract breathable air from snow that overcome many or all of the above-discussed shortcomings in the art.

The apparatus to extract breathable air from snow, in one embodiment, includes an air-permeable extraction assembly, a mouthpiece, and a transfer guide. In a further embodiment, the apparatus may further include an intake valve, a protective helmet, an exhaust chamber, an exhaust tube, a protective membrane, an air transfer channel, and an extraction assembly attachment device.

The air-permeable extraction assembly, in one embodiment, is attached to a backpack. The air-permeable extraction assembly may include at least one air intake cavity and an air-permeable membrane. The air-permeable membrane, in one embodiment, is disposed over the air intake cavity.

The mouthpiece, in one embodiment, is in fluid communication with the at least one air intake cavity. In a further embodiment, the mouthpiece draws intake air through the at least one air intake cavity in response to inhalation by a user.

The transfer guide, in one embodiment, is coupled to the air-permeable extraction assembly and to the mouthpiece. In a further embodiment, the transfer guide passes intake air from the air-permeable extraction assembly to the mouthpiece in response to inhalation by a user. The intake valve, in one embodiment, is disposed between the mouthpiece and the at least one air intake cavity. The intake valve prevents exhaust air exhaled by a user from passing from the mouthpiece to the at least one air intake cavity.

The protective helmet, in one embodiment, may include at least one air intake cavity and the mouthpiece. A protective structure defines an inner cavity and an outer surface of the helmet. A portion of a user's head may be placed within the inner cavity. The air intake cavity or cavities are disposed on the outer surface of the protective structure. The mouthpiece is in fluid communication with the air intake cavity or cavities of the helmet and of the air-permeable extraction assembly of the backpack. Additionally, the mouthpiece is configured to allow a user to draw intake air from ambient snow through the one or more intake cavities and to the user's mouth upon inhalation.

The helmet may be a partial helmet (e.g., an open face helmet) or a full helmet (e.g., a shielded helmet having a protective chin bar). The air intake cavities may be integrally formed within the outer surface of the protective structure, in one embodiment, or separately formed and placed over the protective structure, in another embodiment. Where multiple air intake cavities are provided, they may be connected to one another by one or more air transfer channels. Furthermore, the air intake cavities may be connected to the mouthpiece via one or more of the following: a primary intake cavity, a mouth strap, an intake chamber, a valve, a breathing chamber, and so forth.

In other embodiments, the mouth strap may include the intake chamber, an intake valve, and the breathing chamber. The intake valve prevents exhaust air from passing from the mouthpiece to the at least one air intake cavity. Additionally, the mouth strap may include an exhaust valve and an exhaust chamber. The exhaust valve substantially prevents the user from inhaling exhaust air. The exhaust valve and exhaust chamber pass exhaust air from the mouthpiece and breathing chamber to an exhaust channel upon exhalation by the user. The exhaust channel, in one embodiment, directs the exhaust air away from the at least one intake cavity. For example, the exhaust channel may direct the exhaust air to an exhaust tube configured to extend away from the protective helmet. In one embodiment, the exhaust tube directs the exhaust air to an area of the backpack separated from the air-permeable extraction assembly.

Where the mouth strap includes the intake chamber and the exhaust chamber, these chambers may be disposed on a single side or on opposite sides of the mouthpiece. By disposing the intake chamber and exhaust chambers on a single side of the mouthpiece, the mouth strap may be a partial mouth strap. Alternatively, the mouth strap may be a full mouth strap. In certain embodiments, the mouthpiece may be integrated into a fixed chin bar of the protective helmet. Alternatively, the mouthpiece may be disposed on a mouth strap that is adjustably connected to the protective structure and may be adjusted to move the mouthpiece away from the user's mouth. For example, the mouth strap may be attached to the helmet at one or two points and configured to be rotated upward or downward when the mouthpiece is not engaged by the user.

In a further embodiment, the air-permeable extraction assembly may include the air-permeable membrane interposed between the at least one air intake cavity and a protective membrane. In a further embodiment, the air-permeable extraction assembly may include only the air intake cavities and the air-permeable membrane. In one embodiment, the protective membrane is disposed over at least a portion of the air-permeable extraction assembly. The protective membrane, in a further embodiment, allows air to enter the at least one air intake cavity. In another embodiment, the protective membrane protects the air-permeable membrane from damage and the air-permeable membrane preventing penetration of snow into the at least one air intake cavity.

In one embodiment, the air-permeable extraction assembly of the backpack and/or the protective helmet may comprise multiple air intake cavities. An air transfer channel, in one embodiment, is an enclosed channel that transfers air between the first air intake cavity and the second air intake cavity.

The extraction assembly attachment device, in one embodiment, releasably attaches the air-permeable extraction assembly to the backpack, allowing the air-permeable extraction assembly to at least partially detach from the backpack. In a further embodiment, the extraction assembly attachment device at least partially releases the air-permeable extraction assembly from the backpack in response to impact, such as a user may experience in an avalanche. The extraction assembly attachment device, in one embodiment, may be a snap, a clip, an attachment strap, or an exterior pocket of the backpack.

In one embodiment, the backpack may be an air extraction backpack, and the air-permeable extraction assembly may be integrally attached within an outer lining of the backpack. The air-permeable extraction assembly, in a further embodiment, may be made of a semi-flexible material that bends with the outer lining of the backpack. In another embodiment, the protective membrane may be integrated with an outer surface of the backpack. Further, in one embodiment, the transfer guide may be at least partially embedded within a portion of a carrying strap that is attached to the backpack to allow a user to carry the backpack.

A system to extract breathable air from snow, in one embodiment, includes the backpack and the protective helmet as described above. In one embodiment, the system may include a backpack air-permeable extraction assembly and a helmet air-permeable extraction assembly, with a mouthpiece and a transfer guide. In a further embodiment, a mouth strap, chin strap, fixed chin bar or the like extends from the protective helmet. The mouth strap, chin strap, or fixed chin bar may have an intake chamber configured to pass intake air from a backpack air intake cavity and/or a helmet air intake cavity to the mouthpiece in response to inhalation by a user. In another embodiment, the system includes an extraction apparatus attachment orifice that removably secures the transfer guide to the protective helmet such that the backpack is removable from the protective helmet.

Advantageously, embodiments of the apparatus and system provide a reliable mechanism for drawing air from ambient snow when a user, especially the user's face or head, is at least partially buried in the snow. Additionally, bulky and inefficient breathing tubes are minimized or eliminated.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE INVENTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of materials, shapes, sizes, etc., to provide a thorough understanding of embodiments of the invention. One skilled in the relevant art will recognize, however, that embodiments of the invention can be practiced without one or more of the specific details, or with other methods, components, materials, and so forth. In other instances, well-known structures, materials, or operations are not shown or described in detail to avoid obscuring aspects of the invention.

Figure 1:
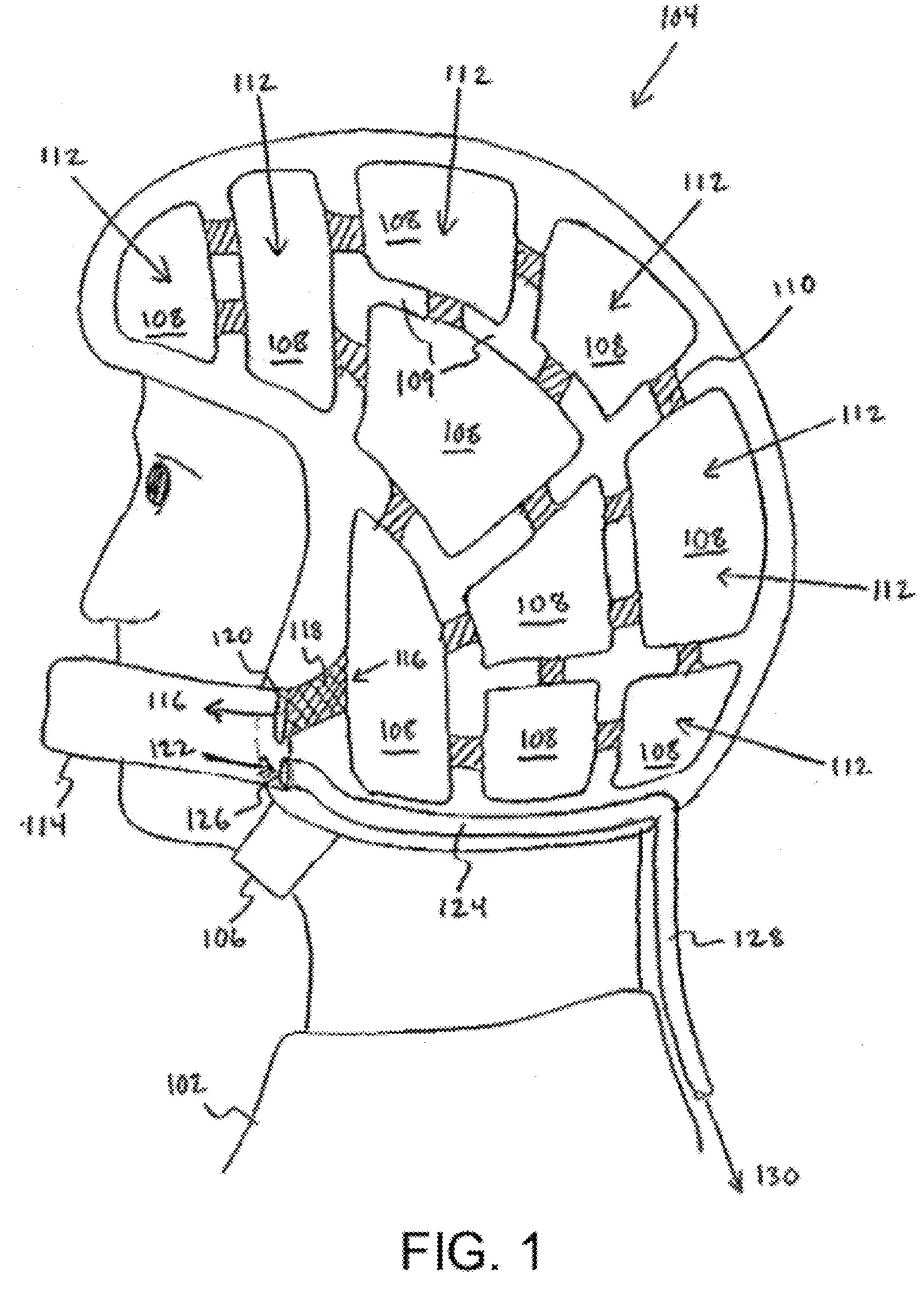
FIG. 1 is a schematic diagram illustrating a cut-away side view one embodiment of a protective helmet for air extraction from snow.

FIG. 1 depicts one embodiment of a user 102 wearing a protective helmet 104 for air extraction from snow. The protective helmet 104 is designed to be worn on the head of the user 102 in a manner similar to other protective headgear, such as full and partial helmets for skiing, snowmobiling, snowshoeing, and other winter sports in which the user 102 may be subject to potential snow burial. In one embodiment, the protective helmet 104 may be worn in place of other protective headgear.

The illustrated protective helmet 104 is secured to the user via a chin strap 106 that is conventionally employed in the art. The protective helmet 104 includes a plurality of air intake cavities 108 that are defined, in one embodiment, by a plurality of cavity dividers 109, such as raised portions or walls. The air intake cavities 108 also may be joined together by one or more air transfer channels 110. In a further embodiment, the air intake cavities 108 may be directly connected to a primary air intake channel 118. The air intake cavities 108 are located on the exterior surface of the protective helmet 104 so that ambient air may enter into the air intake cavities 108 of the protective helmet 104. In one embodiment, the air intake cavities 108 may be large so that few air intake cavities 108 are required over the surface of the protective helmet 104. In an alternate embodiment, the air intake cavities 108 may be small in size and of various shapes, allowing hundreds or even thousands of air intake cavities 108 to be located on the protective helmet 104.

Although a specific size, number, and location of the air intake cavities 108 are illustrated in FIG. 1, the present invention may be embodied in a variety of designs and implementations. For example, the air intake cavities 108 may be located on a specific region of the protective helmet 104, such as the crown, or may be located and separated into groupings of air intake cavities 108 and strategically placed on the protective helmet 104. In one embodiment, the air intake cavities 108 may be located in groupings above and below a goggle strap band region (not shown) that forms an equatorial band around the protective helmet 104.

The illustrated protective helmet 104 also includes a mouth strap 114 that is located over the mouth of the user 102. The mouth strap 114 may be formed with flexible, semi-rigid, or fully rigid material. For example, a ski helmet typically does not have a fully rigid chin bar and the mouth strap 114 may be made of semi-rigid material. In contrast, the mouth strap 114 may be incorporated into a fully rigid chin bar as in the case of a typical snowmobile helmet, for example. The mouth strap 114 is shown in an "engaged" position in which the user 102 is able to breathe through the protective helmet 104 in the event of burial by snow. In one embodiment, the mouth strap 114 may be adjustable for repositioning the mouth strap 114 away from the mouth of the user 102, such as by rotating the mouth strap 114 down below the chin. In another embodiment, the mouth strap 114 may be configured to extend laterally in front of or to the side of the mouth of the user 102 in a "standby" position. In this way, the user 102 may breathe normally without using the breathing features of the protective helmet 104. In a further embodiment, the mouth strap 114 may be in a fixed position. In another embodiment, the mouth strap 114 may be incorporated into a visor. In this way, the mouth strap 114 may serve as a visor while rotated up in the "standby" position and may be rotated downward into the "engaged" position as needed.

In one embodiment, ambient air enters the air intake cavities 108 and passes through the transfer channels 110 as the user 102 inhales. The ambient air may be extracted from surrounding snow in the case where the protective helmet 104 and user 102, for example, are buried in the snow. The user 102 may inhale the intake air, in the direction of the arrows 116, from the air intake cavities 108 through a primary intake channel 118 via an intake orifice 120.

The mouth strap 114 may be configured to allow the user to breathe the inhaled air and subsequently exhale the air, in the direction of the arrow 122 into a primary exhaust channel 124 via an exhaust orifice 126. The depicted protective helmet 104 further includes an exhaust tube 128 that is configured to attach to an opposite side of the primary exhaust channel 124 and direct the exhaled air away from the protective helmet 104 in the direction of the arrow 130. By directing the exhaled air away from the protective helmet, the amount of previously breathed air, if any, that re-enters the air intake cavities 108 is minimized. To minimize or eliminate mixing exhaled air with inhaled air, the air intake cavities 108 located on the exterior of the helmet may be separated from the exit orifice (not shown) of the exhaust tube 128. In one embodiment, this separation may include a minimum distance. Additionally, the separation may be improved by ensuring a barrier, such as the user, between the exit orifice of the exhaust tube 128 and the air intake cavities 108.

For example, in one embodiment, the exhaust tube 128 may direct the exhaled air to the region near the lower back of the user 102. In an alternate embodiment, the exhaust tube 128 may direct the exhaled air to the region near the stomach of the user 102. In a further embodiment, the exhaust tube may be incorporated into the mouth strap 114 or chin strap 106, possibly not requiring a primary exhaust channel 124 or an exhaust orifice 126. In these latter embodiments, the exhaled air may be transferred to the snow in front of the user 102 and still minimize the possibility of mixing the exhaled air with the air surrounding the top, sides, and back of the protective helmet 104.

The exhaust tube 128, in one embodiment, also may be removable from the protective helmet 104. In the case where an exhaust tube 128 is used, the exhaust tube 128 may be secured in place via a garment worn by the user 102, such as a jacket or belt, or by attaching the tube in some fashion to a piece of equipment carried by the user 102, such as a backpack.

Figure 2:
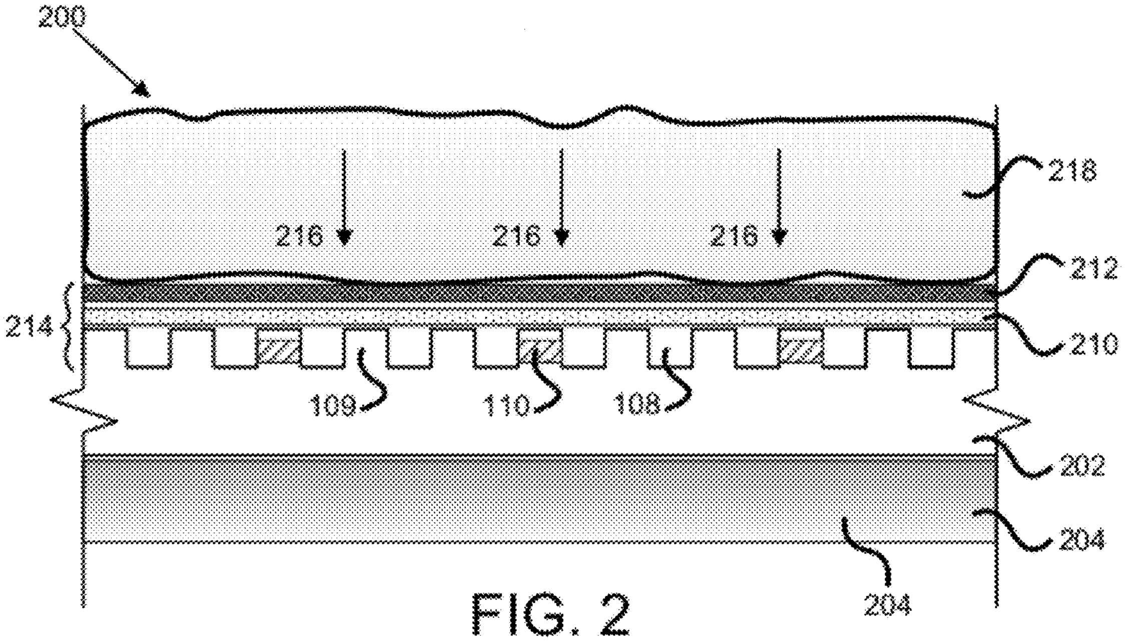
FIG. 2 is a schematic diagram illustrating a sectional view of one embodiment of a portion of a protective helmet for air extraction from snow.

FIG. 2 depicts one embodiment of a cross-section 200 of the protective helmet 104, including a protective structure 202 and a protective lining 204. Although the protective helmet 104 is typically convex in shape to fit the head of the user 102, the depicted protective helmet 104 is shown flat for clarity purposes. The protective structure 202 and protective lining 204 of the present invention are substantially similar to conventionally known protective structures, such as impact foam, and linings conventionally used in helmets. The protective lining 204 is typically located adjacent to the protective structure 202 on the interior of the protective helmet 104. The head of the user 102 is typically placed in contact with the protective lining 204 during normal use of the protective helmet 104.

In the depicted embodiment, the protective helmet 104 also includes a plurality of air intake cavities 108 defined in part by a plurality of cavity dividers 109. The air intake cavities 108 and cavity dividers 109 are generally located on the exterior of the protective structure 202. In one embodiment, the cavity dividers 109 may be formed and located in a manner that provides additional structural protection to the user 102. In an alternative embodiment, the structural integrity of the protective helmet 104 may be unaffected by the design and location of the cavity dividers 109.

The cavity dividers 109 illustrated are attached to or integrally formed as a part of the protective structure 202. Alternately, the cavity dividers 109 may be a wholly separate component and may be placed in contact with the protective structure 202 under a force produced by the air-permeable membrane 210 and/or the protective membrane 212. In other words, the cavity dividers 109 do not need to be integrated with or adhered to the protective structure 202, but may be a separate structure held in place adjacent to the protective structure 202 by the air-permeable membrane 210 and/or the protective membrane 212. In one embodiment, the air intake cavities 108, cavity dividers 109, air-permeable membrane 210, and protective membrane 212 comprise an air-permeable extraction assembly 214.

The air-permeable membrane 210, in one embodiment, is configured to allow ambient air to flow upon inhalation, in the direction of the arrows 216, from the snow 218 (when the protective helmet 104 is buried) to the air intake cavities 108. For example, air may be actively extracted from the surrounding snow through the inhalation efforts of a user 102 buried in snow due to an avalanche. In one embodiment, the air-permeable membrane 210 is impermeable to water, snow, and other similar elements, preventing penetration into the air intake cavities 108. In an alternative embodiment, the air-permeable membrane 210 may allow water or other elements to enter the air intake cavities 108. If water is allowed to enter the air intake cavities 108, the protective helmet 104 may include drainage channels (not shown) that allow the water to exit the air intake cavities 108 prior to entering the mouth strap 114. The air-permeable membrane 210 may be formed from a mesh material, in one embodiment. The protective membrane 212 is configured to protect the air-permeable membrane 210 from damage, such as tearing, due to impact and other use. The protective membrane 212 may include, in one embodiment, a hard impact plastic material that is designed to still allow air to enter the air intake cavities 108. In another embodiment, the protective membrane 212 may be formed from a rip-resistant mesh material.

Figure 3:
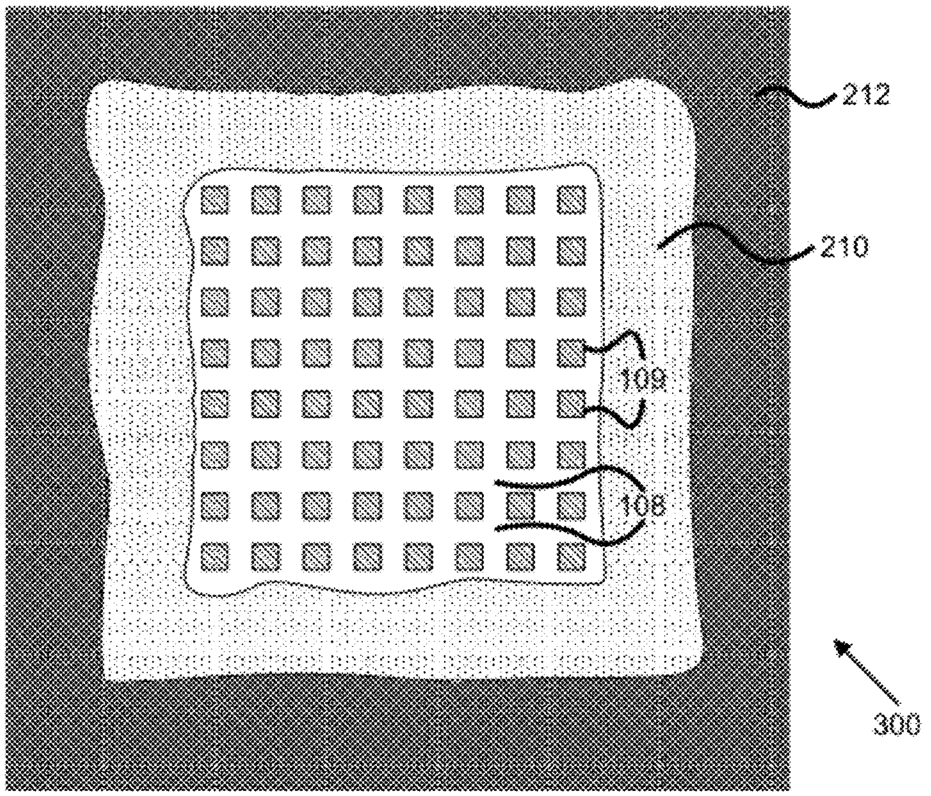
FIG. 3 is a schematic diagram illustrating a cut-away view of one embodiment of a portion of a protective helmet for air extraction from snow.

FIG. 3 depicts one embodiment of a cut-away view 300 of the air-permeable extraction assembly 214, including the air intake cavities 108, cavity dividers 109, air-permeable membrane 210, and protective membrane 212. Specifically, FIG. 3 shows the air intake cavities 108 and cavity dividers 109 underneath the air-permeable membrane 210, which is underneath the protective membrane 212. In the illustrated embodiment, the cavity dividers 109 are located to define air intake cavities 108 in the form of a plurality of parallel and perpendicular channels. In this embodiment, the air-permeable extraction assembly 214 may not require air transfer channels 110 between the various air intake cavities 206.

Figure 4:
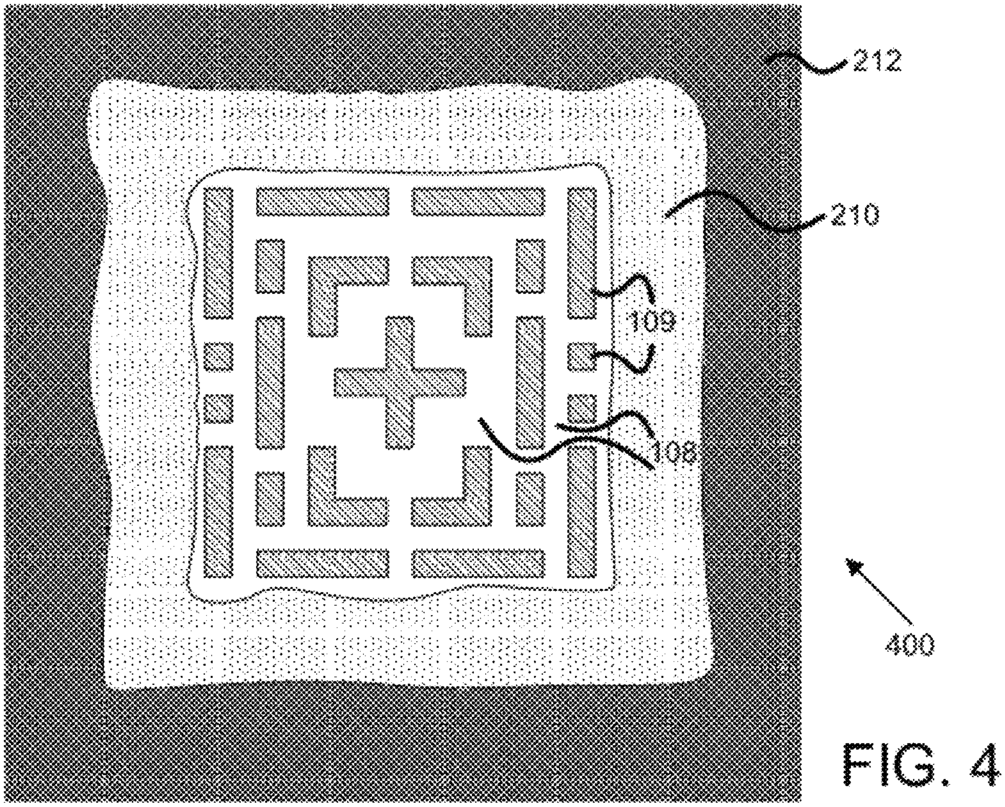
FIG. 4 is a schematic diagram illustrating a cut-away view of an alternate embodiment of a portion of a protective helmet for air extraction from snow.

FIG. 4 depicts a cut-away view 400 of an alternate embodiment of the air-permeable extraction assembly 214. The illustrated embodiment is substantially similar to the embodiment depicted in FIG. 3, except that the cavity dividers 109 are of various shapes and sizes. The cavity dividers 109, in one embodiment, may be placed according to a predetermined pattern, or may be placed at random with respect to one another.

Figure 5:
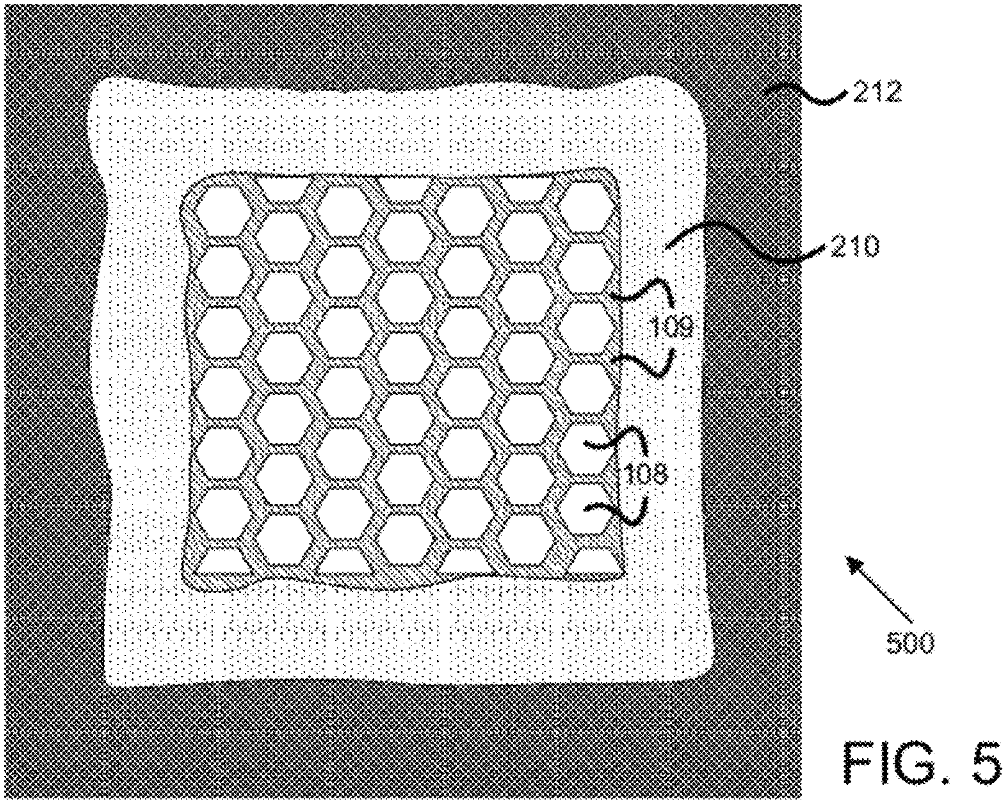
FIG. 5 is a schematic diagram illustrating a cut-away view of an alternate embodiment of a portion of a protective helmet for air extraction from snow.

FIG. 5 depicts a cut-away view 500 of another embodiment of the air-permeable extraction assembly 214 having "honeycomb" cavity dividers 109. In this embodiment, the cavity dividers 109 may form a plurality of air intake cavities 108 that are similar in shape to a honeycomb. Air transfer channels 110, although not shown in FIG. 5, may connect the various air intake cavities 108. In one embodiment, a transfer channel 110 may be formed within a cavity divider 109. In an alternate embodiment, a transfer channel 110 may be formed between the outer surface of the protective structure 202 and the cavity dividers 109. In a further embodiment, a transfer channel 110 may be formed within the protective structure 202. In another embodiment, a transfer channel 110 may be formed within the air-permeable membrane 210. Additionally, the cavity dividers 109 and the air intake cavities 108 may be reversed so that air transfer channels 110 are minimized or not required.

The various embodiments of the air-permeable extraction assembly 214 depicted in FIGS. 3, 4, and 5 may be employed together or separately in helmets for one or more advantages. For example, a particular design for the cavity dividers 109 may increase the structural integrity of the protective structure 202, thereby allowing the thickness of the protective structure 202 to be reduced. Another embodiment of the air-permeable extraction assembly 214 may provide an aesthetic appeal. Furthermore, a particular embodiment of the air-permeable extraction assembly 214 may maximize the surface area of the air intake cavities 108, thereby maximizing the amount of helmet-to-snow surface area and accessibility to a maximum volume of extractable air.

Figure 6:
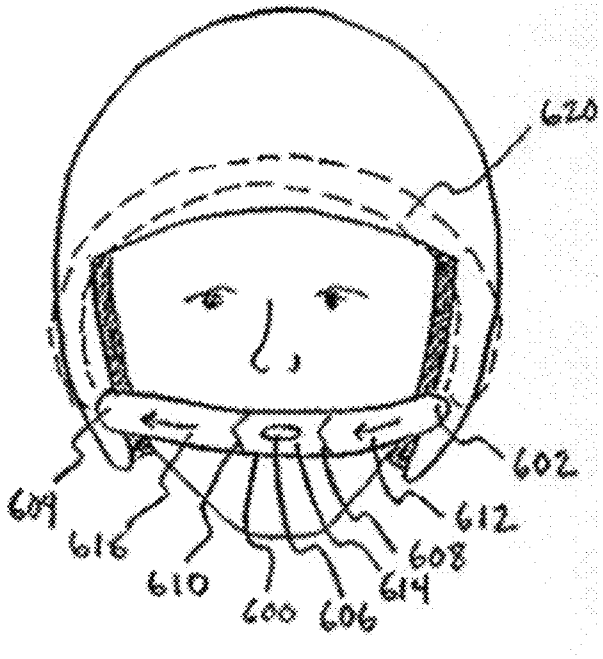
FIG. 6 is a schematic diagram illustrating one embodiment of a protective helmet system for air extraction from snow.

FIG. 6 depicts one embodiment of a full mouth strap 600. The illustrated full mouth strap 600 includes an intake attachment 602 that is configured to be secured to the intake orifice 120 and an exhaust attachment 604 that is configured to be secured to the exhaust orifice 126. The full mouth strap 600 also includes a mouthpiece 606 that is configured to fit into the mouth of the user 102, one or more intake valves 608, and one or more exhaust valves 610. The intake valves 608 and exhaust valves 610 may be located within the mouth strap 600, protective helmet 104, at the intake orifice 120 and exhaust orifice 126, respectively, or distributed throughout the protective helmet 104 and mouth strap 600.

With the mouthpiece 606 in place, the user 102 is able to inhale air through an intake chamber 612, one or more intake valves 608, and a breathing chamber 614. Upon exhaling, the exhaust air exits through the breathing chamber 614, one or more exhaust valves 610, and an exhaust chamber 616. The breathing chamber 614 is preferably designed to limit the amount of exhaled air that is rebreathed by the user 102. For example, the breathing chamber 614 may be designed to hold only a small volume of air, forcing most of the exhaled air to exit through the exhaust chamber 616. The exhaust air travels through the exhaust orifice 126, primary exhaust channel 124, and exhaust tubing 128, as described above. FIG. 6 also depicts the capability of adjusting the mouth strap 114 to a visor standby position 620 (shown dashed) in which the mouthpiece 114 may incorporate and serve as a visor when in the visor standby position 620.

Figure 7:
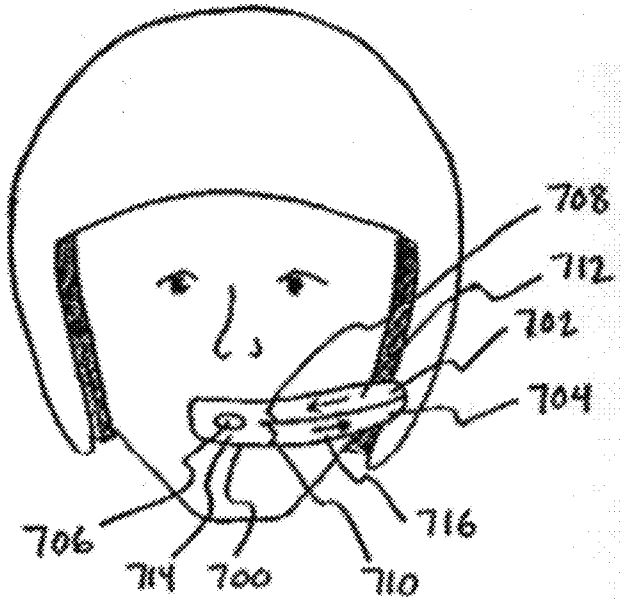
FIG. 7 is a schematic diagram illustrating an alternate embodiment of a protective helmet system for air extraction from snow.

FIG. 7 depicts one embodiment of a partial mouth strap 700 that does not cross the width of the face of the user 102. Instead, the partial mouth strap 700 attaches to only one side of the protective helmet 104 at which both the intake orifice 120 and exhaust orifice 126 are located. The partial mouth strap 700 may comprise a single sheathing for both the intake air and exhaust air, or may comprise separate tubing for each of the intake air and exhaust air.

The illustrated partial mouth strap 700 includes an intake attachment 702 at the intake orifice 120 and an exhaust attachment 704 at the exhaust orifice 126. The partial mouth strap 700 also includes a mouthpiece 706 that is configured to fit into the mouth of the user 102, one or more intake valves 708, and one or more exhaust valves 710. With the mouthpiece 706 in place, the user 102 is able to inhale air through an intake chamber 712, one or more intake valves 708, and a breathing chamber 714. Upon exhaling, the exhaust air exits through the breathing chamber 714, one or more exhaust valves 710, and an exhaust chamber 716. The exhaust air then travels through the exhaust orifice 126, primary exhaust channel 124, and exhaust tubing 128, as described above. Both the full mouth strap 600 of FIG. 6 and the partial mouth strap 700 of FIG. 7 are configured to substantially prevent the user 102 from inhaling exhaust air through the exhaust system and exhaling exhaust air through the intake system, although some exhaust air may be rebreathed from the breathing chamber 614, 714.

Figure 8:
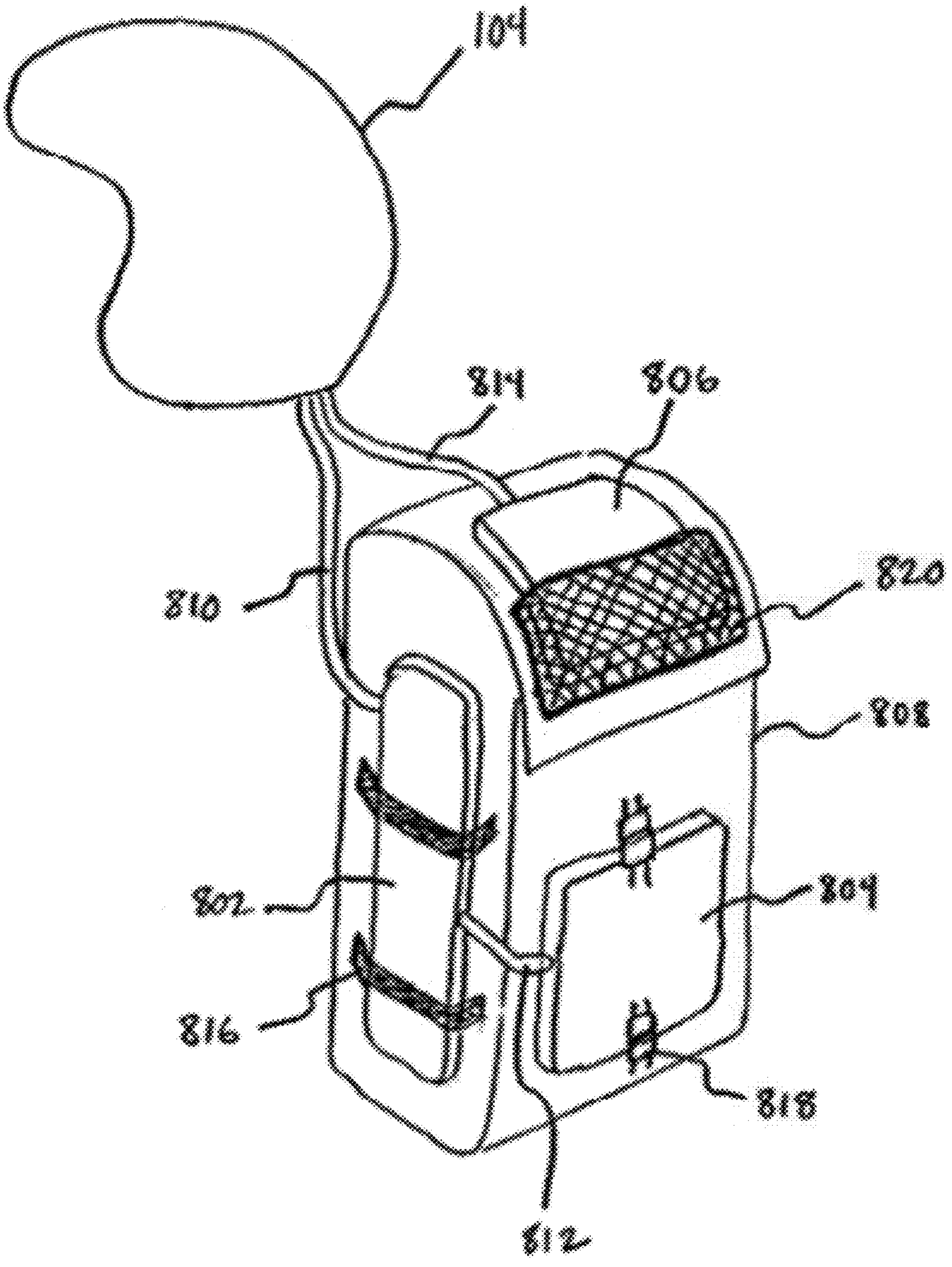
FIG. 8 is a schematic diagram illustrating one embodiment of an extraction apparatus for use with a protective helmet system for air extraction from snow.

FIG. 8 depicts multiple embodiments of an extraction apparatus for use with a protective helmet 104 as described above. Preferably, the extraction apparatus is similar in function to the air-permeable extraction assembly 214 of the protective helmet 104. The illustrated embodiment includes a first extraction apparatus 802, a second extraction apparatus 804, and a third extraction apparatus 806, each separately attached to a backpack 808. Each extraction apparatus 802, 804, 806 is preferably constructed to include a plurality of air intake cavities 108 (not shown) and an air-permeable membrane 210 (not shown). A protective membrane 212 (not shown) may also protect the air intake cavities 108 and air-permeable membrane 210. The air intake cavities 108, air-permeable membrane 210, and protective membrane 212 of the extraction apparatus are substantially similar to the air intake cavities 108, air-permeable membrane 210, and protective membrane 212 of the protective helmet 104 of FIGS. 1 and 2.

The first extraction apparatus 802 also includes a first transfer guide 810 that is configured, in one embodiment, to direct air from the air intake cavities 108 of the first extraction apparatus 802 and the second extraction apparatus 804 to the protective helmet 104 via an extraction apparatus attachment orifice (not shown). The protective helmet 104 or first extraction apparatus 802 may further include a valve (not shown) that is designed to permit flow in a single direction, such as an intake valve within the transfer guide 810.

The second extraction apparatus 804 includes a second transfer guide 812 that, in one embodiment, may be connected to an extraction apparatus attachment orifice (not shown) on the first extraction apparatus 802. In another embodiment of the invention, the second transfer guide 812 may interconnect with the first transfer guide 810 at a point between the air intake cavities 108 of the first extraction apparatus 802 and the protective helmet 104. The illustrated third extraction apparatus 806 includes a third transfer guide 814 that is substantially similar to the first transfer guide 810 and is configured to direct air from the third extraction apparatus 806 to the protective helmet 104, similar to the description above. The second transfer guide 812 and third transfer guide 814 also may include one or more valves (not shown) that permit air flow in a single direction only. The valves of the first, second, and third transfer guides 810, 812, 814 may be located within the transfer guides 810, 812, 814 near the helmet 104 or the backpack 808. Alternately, the valves may be located within the extraction apparatuses 802, 804, 806 or within the protective helmet 102.

The first extraction apparatus 802 is configured, in one embodiment, to be attached to the backpack 808 via one or more adjustable straps 816, such as an adjustable, nylon strap on the side of the backpack 808. The second extraction apparatus 804 is configured, in one embodiment, to be attached to the backpack 808 using conventionally known clips 818, including snaps, clips, and other similar attachments. The third extraction apparatus 806 is configured, in the depicted embodiment, to be attached to the backpack 808 via an exterior pocket 820 of the backpack 808. The exterior pocket 820 is preferably manufactured of nylon mesh or another air-permeable material so that the third extraction apparatus 806 is maximally exposed to the snow when the backpack 808 and third extraction apparatus 806 are buried in the snow.

The extraction apparatuses 802, 804, 806 shown are only exemplary embodiments that may be equivalent to the claimed present invention. Other embodiments may include different shapes and sizes and may be configured to attach to other types of equipment in addition to, or instead of, the backpack 808 shown. For example, a certain embodiment of the invention may include an extraction apparatus configured to be wrapped around the handle or blade of a shovel. In a further embodiment, the invention may include an extraction apparatus integrally attached within the outer lining of the backpack 808 such that the integrated extraction apparatus is contained within a pocket or window of the backpack 808. In one embodiment, the integrated extraction apparatus may be sewn into the backpack 808 in a manner that allows the integrated extraction apparatus to maintain contact or access to the snow in the case of burial by snow. Similarly, the transfer guides 810, 812, 814 may be integrated or sewn into the backpack 808, including the shoulder straps, for additional protection. Furthermore, the extraction apparatus, whether attached to the exterior of the backpack 808 or integrated within the backpack 808, may be made of rigid materials or flexible materials. In one embodiment, the extraction apparatus is made of semi-flexible materials that allow the extraction apparatus to bend and move with the exterior of the backpack 808.

A further embodiment may include an extraction apparatus configured to attach to the equipment at a single point or along a single seam, allowing the extraction apparatus to possibly extend away from the equipment in the case of an avalanche. For example, the second extraction apparatus 804 may be attached to the backpack 808 by a single clip 818, allowing the unattached portion the second extraction apparatus 804 to possibly extend away from the backpack 808. By extending away from the equipment, the extraction apparatus may have a greater surface-to-snow area permitting more air to be extracted from the surrounding snow. In a further embodiment, one of two attachment clips 818 may be a "break-away" clip that is configured to release upon impact, thereby allowing the second extraction apparatus 804 to extend away from the backpack 808.

Although the embodiments set forth in the description above discuss specific examples of implementing the features of the present invention in a protective helmet 104 and a backpack 808, it should be appreciated that one or more extraction apparatuses may be incorporated in another medium other than the specific helmet 104 and backpack 808 presented above. For example, an extraction apparatus may be incorporated into an exterior garment that may be worn by a user. In one embodiment, the air extraction apparatus may be incorporated, such as sewn, into the garment. Alternately, the extraction apparatus may be attached to the exterior of the garment. Similar to the embodiments discussed with reference to FIG. 8, one or more transfer guides may be configured to transfer air from the extraction apparatus to an extraction apparatus attachment orifice of the protective helmet 104.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus to extract breathable air from snow, the apparatus comprising:

an air-permeable extraction assembly attached to a backpack, the air-permeable extraction assembly comprising at least one air intake cavity and an air-permeable membrane, the air-permeable membrane disposed over the air intake cavity, the air-permeable extraction assembly located on an outer surface of the backpack such that the air-permeable extraction assembly is exposed to snow in response to burial of the backpack by the snow;

a mouthpiece in fluid communication with the at least one air intake cavity, the mouthpiece drawing intake air through the at least one air intake cavity in response to inhalation by a user; and a transfer guide coupled to the air-permeable extraction assembly and the mouthpiece, the transfer guide passing intake air from the air-permeable extraction assembly to the mouthpiece in response to inhalation by a user.

2. The apparatus of claim 1, further comprising an intake valve disposed between the mouthpiece and the at least one air intake cavity, the intake valve preventing exhaust air exhaled by a user from passing from the mouthpiece to the at least one air intake cavity.

3. The apparatus of claim 1, further comprising a protective helmet, the transfer guide extending between the at least one air intake cavity and at least one helmet air intake cavity disposed within an outer surface of the protective helmet, the at least one helmet air intake cavity in fluid communication with the mouthpiece.

4. The apparatus of claim 1, further comprising an exhaust chamber in fluid communication with the mouthpiece, the exhaust chamber passing exhaust air from the mouthpiece to an exhaust channel in response to exhalation by a user.

5. The apparatus of claim 4, further comprising an exhaust tube coupled to the exhaust channel and to the backpack, the exhaust tube directing the exhaust air to an area of the backpack separated from the air-permeable extraction assembly.

6. The apparatus of claim 1, further comprising a protective membrane disposed over at least a portion of the air-permeable extraction assembly, the air-permeable membrane interposed between the at least one air intake cavity and the protective membrane, the protective membrane allowing air to enter the at least one air intake cavity and protecting the air-permeable membrane from damage and the air-permeable membrane preventing penetration of snow into the at least one air intake cavity.

7. The apparatus of claim 1, further comprising an air transfer channel, wherein the at least one air intake cavity comprises a first air intake cavity and a second air intake cavity and the air transfer channel comprises an enclosed channel that transfers air between the first air intake cavity and the second air intake cavity.

8. The apparatus of claim 1, further comprising an extraction assembly attachment device that releasably attaches the air-permeable extraction assembly to the backpack, allowing the air-permeable extraction assembly to at least partially detach from the backpack.

9. The apparatus of claim 8, wherein the extraction assembly attachment device at least partially releases the air-permeable extraction assembly from the backpack in response to impact.

10. The apparatus of claim 8, wherein the extraction assembly attachment device is selected from the group consisting of a snap, a clip, an attachment strap, and an exterior pocket.

11. An air extraction backpack to extract breathable air from snow, the air extraction backpack comprising:

a backpack;

a carrying strap attached to the backpack to allow a user to carry the backpack;

an air-permeable extraction assembly disposed on the backpack, the air-permeable extraction assembly comprising at least one air intake cavity and an air-permeable membrane, the air-permeable membrane disposed over the air intake cavity, the air-permeable extraction assembly located on an outer surface of the backpack such that the air-permeable extraction assembly is exposed to snow in response to burial of the backpack by the snow;

a mouthpiece in fluid communication with the at least one air intake cavity, the mouthpiece drawing intake air through the at least one air intake cavity in response to inhalation by a user; and a transfer guide coupled to the air-permeable extraction assembly and the mouthpiece, the transfer guide passing intake air from the air-permeable extraction assembly to the mouthpiece in response to inhalation by a user.

12. The air extraction backpack of claim 11, further comprising an intake valve disposed between the mouthpiece and the at least one air intake cavity, the intake valve preventing exhaust air exhaled by a user from passing from the mouthpiece to the at least one air intake cavity.

13. The air extraction backpack of claim 11, further comprising a protective helmet, the transfer guide extending between the at least one air intake cavity and at least one helmet air intake cavity disposed within an outer surface of the protective helmet, the at least one helmet air intake cavity in fluid communication with the mouthpiece.

14. The air extraction backpack of claim 11, wherein the air-permeable extraction assembly is integrally attached within an outer lining of the backpack.

15. The air extraction backpack of claim 14, wherein the air-permeable extraction assembly comprises a semi-flexible material that bends with the outer lining of the backpack.

16. The air extraction backpack of claim 11, further comprising a protective membrane integrated with an outer surface of the backpack, the protective membrane disposed over at least a portion of the air-permeable extraction assembly, the air-permeable membrane interposed between the at least one air intake cavity and the protective membrane, the protective membrane allowing air to enter the at least one air intake cavity and protecting the air-permeable membrane from damage and the air-permeable membrane preventing penetration of snow into the at least one air intake cavity.

17. The air extraction backpack of claim 11, wherein the transfer guide is at least partially embedded within a portion of the carrying strap.

18. A system to extract breathable air from snow, the system comprising:

a backpack;

a protective helmet;

a backpack air-permeable extraction assembly attached to the backpack, the backpack air-permeable extraction assembly comprising at least one backpack air intake cavity and a backpack air-permeable membrane, the backpack air-permeable membrane disposed over the backpack air intake cavity, the air-permeable extraction assembly located on an outer surface of the backpack such that the air-permeable extraction assembly is exposed to snow in response to burial of the backpack by the snow;

a helmet air-permeable extraction assembly disposed within an outer surface of the protective helmet, the helmet air-permeable extraction assembly comprising at least one helmet air intake cavity and a helmet air-permeable membrane, the helmet air-permeable membrane disposed over the helmet air intake cavity;

a mouthpiece in fluid communication with at least one of the backpack and helmet air intake cavities, the mouthpiece drawing intake air through at least one of the backpack and helmet air intake cavities in response to inhalation by a user; and a transfer guide extending between the helmet air-permeable extraction assembly and the backpack air-permeable extraction assembly, the transfer guide in fluid communication with the mouthpiece, the transfer guide passing intake air from at least one of the helmet and backpack air-permeable extraction assemblies to the mouthpiece in response to inhalation by a user.

19. The system of claim 18, further comprising one of a mouth strap, chin strap, and fixed chin bar extending from the protective helmet and having an intake chamber configured to pass intake air from at least one of the backpack and helmet air intake cavities to the mouthpiece in response to inhalation by a user.

20. The system of claim 18, further comprising an extraction apparatus attachment orifice that removably secures the transfer guide to the protective helmet such that the backpack is removable from the protective helmet.

* * * * *